United States Patent
Cannell et al.

(10) Patent No.: US 10,311,352 B2
(45) Date of Patent: Jun. 4, 2019

(54) HEALTHCARE BEACON DEVICE CONFIGURATION SYSTEMS AND METHODS

(71) Applicants: General Electric Company, Schenectady, NY (US); ZIH Corp., Lincolnshire, IL (US)

(72) Inventors: Matthew James Cannell, Glen Allen, VA (US); David Nguyen, Morgan Hill, CA (US); Edward Geiger, San Martin, CA (US); Mahender Vangati, San Jose, CA (US); Richard Woodburn, Cupertino, CA (US)

(73) Assignees: General Electric Company, Schenectady, NY (US); ZIH Corp., Lincolnshire, IL (US)

( * ) Notice: Subject to any disclaimer, the term of this patent is extended or adjusted under 35 U.S.C. 154(b) by 0 days.

(21) Appl. No.: 15/945,424

(22) Filed: Apr. 4, 2018

(65) Prior Publication Data
US 2018/0293478 A1 Oct. 11, 2018

Related U.S. Application Data

(63) Continuation-in-part of application No. 15/481,217, filed on Apr. 6, 2017.

(51) Int. Cl.
*G06K 19/07* (2006.01)
*G16H 40/40* (2018.01)

(52) U.S. Cl.
CPC ......... *G06K 19/0723* (2013.01); *G16H 40/40* (2018.01)

(58) Field of Classification Search
None
See application file for complete search history.

(56) References Cited

U.S. PATENT DOCUMENTS 7,586,413 B2 9/2009 Davis
8,319,635 B2 11/2012 Perkins et al.
(Continued)

OTHER PUBLICATIONS

United States Patent and Trademark Office, "Non-Final Office action," issued in connection with U.S. Appl. No. 15/481,217, dated Sep. 29, 2017, 17 pages.
(Continued)

*Primary Examiner* — David Bilodeau
(74) *Attorney, Agent, or Firm* — Hanley, Flight and Zimmerman, LLC

(57) ABSTRACT

Beacon devices and associated components, methods, etc., are disclosed. An example beacon device includes a memory, a communication interface, and a processor to execute instructions with respect to configuration information to control the communication interface and operation of the processor based on a mode in which the beacon device is set to operate, the processor to dynamically transition among a plurality of modes based on an operating condition of the beacon device and a communication received from at least one of the receiver or the controller. In certain examples, the plurality of modes includes a configuration mode and a broadcast mode. When in the configuration mode, the operation of the processor is to process the communication received from the controller to adjust the configuration information. When in the broadcast mode, the operation of the processor is to generate a beacon signal to transmit to at least one of the receiver or the controller via the communication interface.

20 Claims, 10 Drawing Sheets

(56) References Cited

U.S. PATENT DOCUMENTS

| | | |
|---|---|---|
| 8,457,656 B2 | 6/2013 | Perkins et al. |
| 8,712,330 B2 | 4/2014 | Desai et al. |
| 8,762,519 B2 | 6/2014 | Thomson et al. |
| 8,847,754 B2 | 9/2014 | Buchheim et al. |
| 8,949,782 B2 | 2/2015 | Shang et al. |
| 9,031,577 B2 | 5/2015 | Mirzaei et al. |
| 9,277,018 B2 | 3/2016 | Kotecha et al. |
| 9,374,667 B1 | 6/2016 | Jorgensen et al. |
| 9,848,383 B2 | 12/2017 | Kochery et al. |
| 9,892,351 B2 | 2/2018 | Connolly et al. |
| 2009/0055854 A1 | 2/2009 | Wright et al. |
| 2014/0135042 A1 | 5/2014 | Buchheim et al. |
| 2014/0370917 A1 | 12/2014 | Buchheim et al. |
| 2015/0133170 A1 | 5/2015 | Buchheim et al. |
| 2016/0088421 A1 | 3/2016 | Warner et al. |
| 2016/0127875 A1 | 5/2016 | Zampini, II |
| 2016/0136312 A1 | 5/2016 | Park et al. |
| 2016/0209655 A1 | 7/2016 | Riccomini et al. |
| 2016/0324442 A1 | 11/2016 | Zdeblick |
| 2018/0025607 A1 | 1/2018 | Sundaram et al. |
| 2018/0027384 A1 | 1/2018 | Sundaram et al. |

OTHER PUBLICATIONS

United States Patent and Trademark Office, "Final Office action," issued in connection with U.S. Appl. No. 15/481,217, dated Mar. 28, 2018, 22 pages.

HEALTHCARE BEACON DEVICE CONFIGURATION SYSTEMS AND METHODS

CROSS-REFERENCE TO RELATED APPLICATIONS

This patent claims priority as a continuation-in-part to U.S. Non-Provisional application Ser. No. 15/481,217, entitled "HEALTHCARE ASSET BEACON," filed on Apr. 6, 2017, which is hereby incorporated by reference in its entirety.

FIELD OF THE DISCLOSURE

This disclosure relates generally to tracking beacons, and, more particularly, to healthcare asset beacons and beacon configuration.

BACKGROUND

Real-time location systems (RTLS) monitor asset distribution and usage, providing actionable information to help control costs and improve the quality and efficiency of care. Systems that have been developed to track and analyze activities in clinical settings have included installing Radio Frequency Identification (RFID) or infrared (IR) reader infrastructures into buildings to capture position information. RFID sensors may be placed on the people and/or assets that need to be tracked.

However, this is an expensive and time-consuming solution because it requires pulling power and data cabling to all the required locations. Location accuracy can also vary depending on technology. Typical RFID systems have a tolerance of approximately plus-or-minus ten feet, further limiting their range. RFID and IR-based sensors, though, are highly susceptible to drift due to interference in the environment (e.g., a patient room) and cross talk between locations that are physically separated but have a line of sight between them (e.g., two patient rooms across the hall from each other).

Therefore, it would be desirable to design a system and method for tracking locations and interactions between people and assets in an environment with minimal infrastructure requirements and standardized technologies.

BRIEF DESCRIPTION

Certain examples provide beacon devices and associated components, methods, etc. An example low-power, short-range radio frequency wireless beacon device includes a memory to store instructions and configuration information and a communication interface to communicate with at least one of a receiver or a controller. The example beacon device also includes a processor to execute the instructions with respect to the configuration information to control the communication interface and operation of the processor based on a mode in which the beacon device is set to operate, the processor to dynamically transition among a plurality of modes based on an operating condition of the beacon device and a communication received from at least one of the receiver or the controller. In certain examples, the plurality of modes includes a configuration mode and a broadcast mode. When in the configuration mode, the operation of the processor is to process the communication received from the controller to adjust the configuration information. When in the broadcast mode, the operation of the processor is to generate a beacon signal to transmit to at least one of the receiver or the controller via the communication interface.

An example at least one non-transitory medium includes instructions which, when executed, cause at least one processor in a beacon device to at least execute the instructions with respect to configuration information to control a communication interface and operation of the at least one processor based on a mode in which the beacon device is set to operate. In certain examples, the processor is to dynamically transition among a plurality of modes based on an operating condition of the beacon device and a communication received from at least one of a receiver or a controller, wherein the plurality of modes includes a configuration mode and a broadcast mode. When in the configuration mode, the operation of the at least one processor is to process the communication received from the controller to adjust the configuration information. When in the broadcast mode, the operation of the at least one processor is to generate a beacon signal to transmit to at least one of the receiver or the controller via the communication interface.

An example method of controlling a beacon device including at least one processor and a communication interface includes executing, using the at least one processor, instructions with respect to configuration information to control the communication interface and operation of the at least one processor based on a mode in which the beacon device is set to operate. In certain examples, the beacon device is to dynamically transition among a plurality of modes based on an operating condition of the beacon device and a communication received from at least one of the receiver or the controller, the plurality of modes including a configuration mode and a broadcast mode. The example method includes, when in the configuration mode, processing, using the at least one processor, communication received from the controller to adjust the configuration information. The example method includes, when in the broadcast mode, generating, using the at least one processor, a beacon signal to transmit to at least one of the receiver or the controller via the communication interface.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

DETAILED DESCRIPTION

Figure 1:
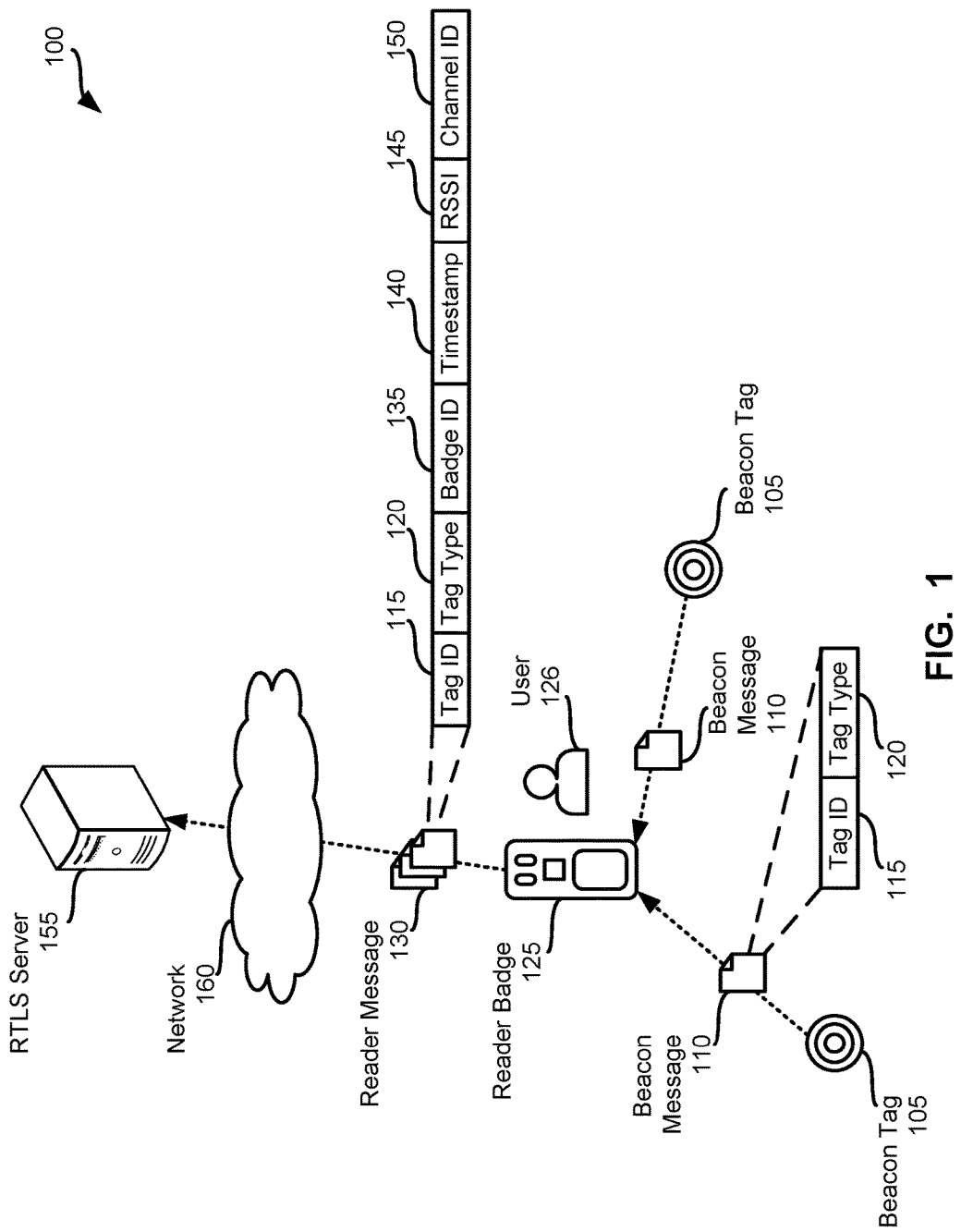
FIG. 1 is a block diagram illustrating an example environment constructed in accordance with the teachings of this disclosure to facilitate proximity detection and location tracking.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

I. Overview

Certain examples of the presently disclosed technology improve proximity detection and location tracking of resources in an environment such as a hospital. An example system disclosed herein includes one or more beacon tags affixed to assets within the environment and that transmit (e.g., periodically, aperiodically and/or as a one-time event) beacon messages. The beacon messages are received by a mobile reader badge that listens for beacon messages transmitted in the environment. For example, disclosed example reader badges (sometimes referred to herein as "readers," "badges," "mobile wireless bridges," or "beacon badges") may include a network interface to receive beacon messages transmitted via low power Bluetooth Low Energy (BLE) and/or other low-power, short-range radio frequency wireless communication. In some disclosed examples, the reader badges process the received beacon messages and communicate information obtained from the beacon messages to one or more real-time location services (RTLS) servers via a communication infrastructure. For example, disclosed example reader badges may aggregate and communicate a batch of beacon messages (e.g., a threshold number of beacon messages, a threshold interval of time (e.g., a window of interest), etc.) to an RTLS server via a Wi-Fi infrastructure (e.g., a wireless network). In some disclosed examples, the RTLS server processes the received batch of beacon messages to facilitate real-time location tracking of the resources in the environment. In some disclosed examples, the RTLS server may report the location of resources via charts, graphs, tables, etc.

Real-time location services enable improved patient workflow via proximity detection and location tracking in a healthcare environment, such as a hospital. Location tracking can be used to locate resources such as mobile assets (e.g., patients, intravenous (IV) pumps, telemetry units, wheelchairs, etc.) within the hospital. For example, location tracking can be used to locate a "lost" or "missing" IV pump within a patient's room. Proximity detection facilitates an improved understanding of how interactions occur during the patient workflow. For example, based on the proximity to a soap dispenser, a user (e.g., a system administrator) can determine whether a caretaker washed their hands prior to interacting with a patient.

Examples systems and methods disclosed herein facilitate improved proximity detection and location tracking by creating a hospital tracking network within the hospital using the communication infrastructure already installed in the hospital. Beacon tags are installed throughout a location or building. For example, beacon tags can be affixed to stationary assets (e.g., patient room entry ways, sinks, water fountains, hallways, etc.) and mobile assets such as hospital beds, IV pumps, soap dispensers, etc. In some disclosed examples, the beacon tags are also included in disposable patient tags provided to the patient upon admission of a hospital stay. Beacon tags are low-cost, low-power transmitters of beacon messages. A beacon message (sometimes referred to herein as a "beacon") includes information about the beacon tag such as a unique identifier (e.g., a tag identifier such as a media access control (MAC) address) and a tag type identifier (e.g., whether the beacon tag is affixed to a fixed-location asset or to a mobile asset). In some disclosed examples, the beacon tags broadcast (e.g., advertise, communicate, transmit, etc.) beacon messages at pre-set frequencies (e.g., ten times a second, once a second, once a minute, etc.). For example, a beacon tag affixed to a fixed-location asset (e.g., a sink) may broadcast beacon messages ten times a second, while a beacon tag affixed to a mobile asset (e.g., a wheelchair) may broadcast beacon messages at relatively shorter intervals (e.g., once a second).

A reader badge is a mobile wireless bridge that facilitates mobile tracking by "listening" and receiving beacon messages broadcast by beacon tags. The reader badge includes a BLE controller (and/or other low-power, short-range radio frequency wireless controller) to receive connection-less beacon messages broadcast by beacon tags. The reader badge also includes a Wi-Fi controller to establish a connection with an RTLS server. The reader badge may be worn or transported by hospital caregivers. For example, a reader badge may be worn as a lanyard or clipped to the caregiver's clothing. As the caregiver moves about the hospital, the reader badge passively collects beacon messages and communicates reader messages to an RTLS server at the backend of the system. In some examples, the reader badge collects a number (e.g., a predetermined number) of beacon messages or waits a period (e.g., a predetermined period of time) prior to communicating the reader messages. In some examples, the reader badge generates and communicates a reader message as a beacon message from a beacon tag is received. A reader message includes information received from the beacon message such as a unique identifier of the source beacon tag and a spatial location of the source beacon tag. In some examples, the reader badge includes a timestamp identifying when the beacon message was received by the reader badge in the reader message. In some examples, the reader badge includes a received signal strength indication (RSSI) value (e.g., a power ratio in decibels of the measured power to one milli-watt (dBm)).

Example reader badges disclosed herein include a proximity engine to process the beacon messages and determine distance from the source (e.g., the beacon tag that broadcast the corresponding beacon message). For example, a hospital room may include a first beacon tag affixed to a door, a second beacon tag affixed to an infusion pump, a third beacon tag affixed to a bed, and a fourth beacon tag included in a patient tag (e.g., a disposable bracelet including patient identification information such as name, sex, date of birth information). As the caregiver moves about the hospital room, the reader badge may receive beacon messages from each of the beacon tags. The proximity engine can determine the RSSI strength for each of the beacon messages and associate RSSI strength with a respective beacon tag.

In some examples, the proximity engine determines which beacon tags are proximate (e.g., near or closely located) to the reader badge. For example, the proximity engine can compare the RSSI strength of a beacon message to a threshold and if the RSSI strength satisfies the threshold (e.g., the RSSI strength is greater than a threshold), the proximity engine identifies the source beacon tag as proximate to the reader badge. In some examples, the proximity engine discards beacon messages that are not proximate to the reader badge.

Example systems and methods disclosed herein include an RTLS server that monitors and/or reports tracking location and interactions between people and assets in an environment. For example, the RTLS server can aggregate reader messages from the one or more reader badges included in an environment (e.g., the hospital). The RTLS server may be in connection with the reader badges via a wireless Intranet network (e.g., a wireless local area network, etc.) and/or a wireless Internet connection.

As healthcare assets continue to become smaller and more ergonomic, RTLS tracking with a small footprint becomes increasingly important. Additionally, as a hospital's inventory of healthcare equipment gets leaner, the equipment is likely to be cleaned more often. Therefore, an asset tracking beacon should withstand frequent, repeated cleaning with harsh disinfecting chemicals.

Certain examples provide an improved housing that can be applied with BLE and/or other low-power, short-range radio frequency wireless location tracking technology to healthcare assets (e.g., scanner, IV pumps, monitors, etc.). In certain examples, a computerized maintenance management system (CMMS) and/or source system can organize and monitor assets and can remove and re-associate beacons from one asset to another asset on demand. Beacons can be installed on ergonomic items that do not have flat surfaces. Beacons can be developed with housings to withstand rigorous healthcare cleaning protocols while maintaining a small footprint to not disturb normal usage of equipment to which the beacon is applied.

II. Example Hospital Tracking Network

Real-time location services (RTLS) facilitate tracking people and assets in an industrial setting, such as a hospital. The example RTLS system described herein is designed to create location awareness of assets by capturing location and proximity information from beacon tags installed throughout the hospital. Examples disclosed herein utilize reader badges worn by healthcare workers (e.g., doctors, nurses, administrators, janitors, etc.) that receive beacon messages from beacon tags that are installed in and/or affixed to assets such as hallways, rooms, equipment, patients, etc. for which location and/or proximity information is to be collected between the beacon tags and the tagged asset. For example, the beacon tags may broadcast beacon messages including a unique identifier (e.g., a signature, a media access control (MAC) address, a serial number, etc.) associated with the corresponding beacon tags. As the healthcare workers walk around the hospital, their reader badges collect beacon messages transmitted from beacon tags throughout the hospital. In some disclosed examples, the reader badges aggregate the beacon messages and transmit a batch of beacon messages to an RTLS server for processing. The example RTLS server disclosed herein processes the beacon messages to create location awareness through proximity and probability.

In some disclosed examples, beacon tags are installed in and/or attached to fixed-location (e.g., placed on stationary (or near stationary)) assets. For example, some "known location" beacon tags may be affixed to hallways, doors, windows, sinks, etc. As disclosed below, in some examples, the RTLS server utilizes the beacon messages received from "known location" beacon tags to determine a location for the reader badge.

In some disclosed examples, beacon tags are affixed to mobile assets such as equipment. For example, some "mobile location" beacon tags may be affixed to beds, wheelchairs, patients, etc. As disclosed below, in some examples, the RTLS server utilizes the beacon messages received from the "mobile location" beacon tags to determine what assets are near the corresponding reader badges (e.g., the reader badge that aggregated and transmitted a batch of beacon messages).

In addition, comparing the asset locations during different timestamp intervals may be useful in determining how the assets were moved and/or when caregivers interacted with the assets. For example, consider an example in which a wheelchair (e.g., a mobile-location asset) is located in a first patient room. In the illustrated example, assume that the wheelchair is affixed with a mobile-location asset beacon tag and that the first patient room is affixed with a fixed-location asset beacon tag. In the illustrated example, when a caregiver wearing a reader badge walks into the first patient room, their reader badge collects beacon messages broadcast by the wheelchair beacon tag and the first patient room beacon tag. In the illustrated example, the caregiver location is assigned to the first patient room based on the beacon messages broadcast by the first patient room beacon tag. In addition, since the wheelchair is "seen" in the same location, the wheelchair location may also be updated to the first patient room.

In the illustrated example, while the caregiver is in the first patient room, their reader badge collects beacon messages broadcast by the wheelchair beacon tag and the first patient room beacon tag. If the caregiver begins moving the wheelchair (e.g., from the first patient room to a second patient room), their reader badge will continue to collect beacon tags broadcast by the first patient room badge tag but will also begin collecting beacon messages broadcast by a second patient room beacon tag. In the illustrated example, once the caregiver enters the second patient room, the caregiver location is updated to the second patient room. Additionally, in the illustrated example, since the wheelchair is still "seen" by the caregiver (e.g., the wheelchair location is determined to be proximate to the caregiver), the location of the wheelchair is also updated to the second patient room.

In the illustrated example, after the wheelchair is moved from the first patient room to the second patient room, confidence that the wheelchair is located in the second patient room rather than the first patient room may be low. However, in the illustrated example, each time a caregiver walks into the first patient room and does not "see" the wheelchair, confidence that the wheelchair is located in the first patient room decreases. Additionally, in the illustrated example, each time a caregiver walks into the second patient room and does "see" the wheelchair, confidence that the wheelchair is located in the second patient room increases. In the illustrated example, the "crowd" (e.g., the caregivers) provides different snapshots of what is "seen" at different locations and at different times. As disclosed herein, an RTLS server may analyze the different snapshots to facilitate proximity detection and location tracking of assets in an environment.

Referring to FIG. 1, an example environment 100 in which examples disclosed herein may be implemented to facilitate proximity detection and location tracking using a mobile wireless bridge is illustrated. The example environment 100 of FIG. 1 includes example beacon tags 105, an example reader badge 125 and an example real-time location services (RTLS) server 155.

In the illustrated example of FIG. 1, the beacon tags 105 are implemented using low-power BLE or other low-power, short-range radio frequency wireless transmitters and include a single coin-cell battery. In some examples, the single coin-cell battery provides power to the corresponding beacon tag 105 for two or more years. In the illustrated example, beacon tags 105 are installed throughout the environment 100 on two types of assets. For example, one or more beacon tag(s) 105 may be located on (e.g., affixed to) fixed-location assets such as doors, rooms, hallways, water fountains, etc. In addition, one or more beacon tag(s) 105 may be located on (e.g., affixed to) mobile-location assets such as patients (e.g., inserted within a patient tag), beds, IV pumps, wheelchairs, etc. Although the illustrated example of FIG. 1 includes only two beacon tags 105, other environments are likely to include additional beacon tags. For example, different environments may include tens, hundreds and/or thousands of beacon tags affixed to assets. In general, accuracy of the proximity detection and location tracking of assets in an environment is increased and/or decreased based on adding or reducing the number of beacon tags placed in the environment.

In the illustrated example of FIG. 1, the example beacon tags 105 periodically advertise their presence in the environment 100. For example, the beacon tags 105 may broadcast example beacon messages 110 every one second. In other examples, the beacon tags 105 may broadcast beacon messages 110 aperiodically and/or as a one-time event. In some examples, the beacon tags 105 may broadcast beacon messages 110 at different time intervals. For example, beacon tags 105 located on fixed-location assets may broadcast beacon messages 110 every two seconds, while beacon tags 105 located on mobile-location assets may broadcast beacon messages 110 every second. In some examples, beacon tags located on mobile-locations assets may broadcast beacon messages 110 at a first frequency (e.g., once every second) while the mobile-location asset is stationary and may broadcast beacon messages 110 at a second frequency (e.g., once every half-second) while the mobile-location asset is moving. However, other time intervals may additionally or alternatively be used.

In the illustrated example, the beacon messages 110 include tag identifying information 115 and tag-type identifying information 120. For example, tag identifying information 115 may be a unique identifier of the beacon tag 105 such as a MAC address, a serial number, an alphanumeric signature, etc. The example tag-type identifying information 120 identifies whether the beacon tag 105 broadcasting the beacon message 110 is affixed to a fixed-location asset or affixed to a mobile-location asset. However, the beacon messages 110 may include additional or alternative information. For example, the beacon messages 110 may include information identifying the software version being executed by the beacon tags 105, may include information identifying a power level of the beacon tag 105, etc.

In the illustrated example of FIG. 1, the beacon messages 110 are received by the reader badge 125. In the illustrated example, the reader badge 125 is worn by a hospital caregiver 126 such as a doctor, a nurse, etc. As the hospital caregiver moves through the hospital, the reader badge 125 collects beacon messages 110 broadcast by the beacon tags 105. For example, while the hospital worker 126 is visiting a patient in an example patient room #1, the example reader badge 110 may collect one or more beacon message(s) from a fixed-location asset beacon tag located on a door of the patient room #1, one or more beacon message(s) from a fixed-location asset beacon tag located on a sink in the patient room #1, one or more beacon message(s) from a mobile-location asset beacon tag located on the patient's identification tag, one or more beacon message(s) from a mobile-location asset beacon tag located on a bed in the patient room #1, etc.

In the illustrated example of FIG. 1, the reader badge 125 generates example reader messages 130 in response to receiving the beacon messages 110. For example, the reader badge 125 may create a reader message 130 including the tag identifying information 115 and the tag-type identifying information 120 included in the beacon message 110 and append example badge identifying information 135, an example timestamp 140, example signal strength information 145, and example channel identifying information 150. In the illustrated example, the badge identifying information 135 is a string of alphanumeric characters that uniquely identifies the reader badge 110 (e.g., a MAC address, a serial number, an alphanumeric signature, etc.). The example timestamp 140 identifies a date and/or time (e.g., January 1, 2015, 9:10:04 pm) when the beacon message 110 was received by the reader badge 125. The example signal strength information 145 identifies signal strength of the beacon message 110 when it was received by the reader badge 125 (e.g., a received signal strength indication (RSSI) value). The example channel identifying information 150 identifies a channel on which the beacon message 110 was received (e.g., a Bluetooth and/or other low-power, short-range radio frequency wireless frequency channel such as channel 37, channel 38 or channel 39, etc.).

In the illustrated example of FIG. 1, the reader badge 125 periodically communicates a group (e.g., a batch) of reader messages 130 to the RTLS server 155. For example, the reader badge 125 may transmit one or more reader messages 130 that were collected over a period of time (e.g., thirty seconds). Additionally or alternatively, the reader badge 125 may communicate one or more reader message(s) 130 aperiodically and/or as a one-time event. For example, the reader badge 125 may collect a threshold number of reader messages 130 prior to transmitting the collected reader messages 130 to the RTLS server 155. In some examples, the reader badge 125 transmits the reader messages 130 as they are created by the reader badge 125.

In the illustrated example of FIG. 1, the RTLS server 155 is a server and/or database that facilitates proximity detection and location tracking. In some examples, the RTLS server 155 is implemented using multiple devices. For example, the RTLS server 155 may include disk arrays or multiple workstations (e.g., desktop computers, workstation servers, laptops, etc.) in communication with one another.

In the illustrated example, the RTLS server 155 is in communication with the reader badge 125 via one or more wireless networks represented by example network 160. Example network 160 may be implemented using any suitable wireless network(s) including, for example, one or more data busses, one or more wireless Local Area Networks (LANs), one or more cellular networks, the Internet, etc. As used herein, the phrase "in communication," including variances thereof (e.g., communicates, in communication with, etc.), encompasses direct communication and/or indirect communication through one or more intermediary components and does not require direct physical (e.g., wired) communication and/or constant communication, but rather additionally includes communication at periodic or aperiodic intervals, as well as one-time events.

In the illustrated example of FIG. 1, the RTLS server 155 utilizes the reader messages 130 to facilitate proximity detection and location tracking of assets in the environment 100. In the illustrated example, the RTLS server 155 selects a portion of reader messages 130 received from the reader badge 125 to determine a location of the reader badge 125. For example, the RTLS server 155 may process the reader messages 130 to identify a first subset of reader messages 130 (e.g., one or more reader messages) that were received by the reader badge 125 during a first window of interest (e.g., a five second window) and that were fixed-location asset tag type (e.g., based on the tag-type information 120 included in the first subset of reader messages). In the illustrated example of FIG. 1, the RTLS server 155 utilizes the signal strength information 145 included in the first subset of reader messages 430 to determine a nearest fixed-location asset. For example, a relatively stronger RSSI value may indicate that the broadcasting beacon tag 105 is closer in proximity to the reader badge 125 than a beacon tag 105 associated with a relatively weaker RSSI value. In the illustrated example of FIG. 1, the RTLS server 155 updates the location of the reader badge 125 based on the nearest fixed-location asset.

In the illustrated example of FIG. 1, once the RTLS server 155 associates the reader badge 125 with a location (e.g., the location of the nearest fixed-location asset, etc.), the RTLS server 155 identifies a second subset of reader messages 130 (e.g., one or more reader messages, etc.) that were received by the reader badge 125 during the first window of interest (e.g., a five second window, etc.) and that were mobile-location asset tag type (e.g., based on the tag-type information 120 included in the second subset of reader messages 130, etc.). For example, the RTLS server 155 may update the location of a mobile-location asset based on its proximity to the reader badge 125.

In the illustrated example of FIG. 1, the RTLS server 155 selects a reader message of the second subset of reader messages 130 and classifies the corresponding mobile-location assets relative location to the reader badge 125 based on the RSSI value 155 included in the selected reader badge 130. For example, the RTLS server 155 classifies mobile-location asset as relatively-far assets when the signal strength information 155 satisfies a first threshold (e.g., the RSSI value is less than (−60) decibels, etc.). The example RTLS server 155 of FIG. 1 classifies mobile-location assets as relatively-immediate assets when the signal strength information 155 satisfies a second threshold (e.g., the RSSI value is greater than (−40) decibels, etc.). In the illustrated example of FIG. 1, the RTLS server 155 classifies mobile-location assets as relatively-near assets when the signal strength information 155 does not satisfy the first threshold and the second threshold. For example, the RTLS server 155 may classify mobile-location assets as relatively-near assets when the RSSI value is less than (−40) decibels and greater than (−60) decibels.

In the illustrated of FIG. 1, depending on the relative location classifications, the RTLS server 155 updates the location of the mobile-location asset and/or updates an asset-location confidence score associated with the mobile-location asset. In the illustrated example, the asset-location confidence score represents a probability (or likelihood) that a mobile-location asset may be found at the currently assigned asset-location. For example, when a mobile-location asset is "seen" in the same location, the RTLS server 155 increases the asset-location confidence score of the mobile-location asset. When the mobile-location asset is "seen" in a different location, the RTLS server 155 decreases the asset-location confidence score of the mobile-location asset. Additionally, when the asset-location confidence score fails to satisfy a location threshold (e.g., is less than a location threshold, etc.), the asset-location of the mobile-location asset may be updated based on, for example, the location of the reader badge 125 that collected the beacon message 110 emitted from the mobile-location asset (e.g., by the beacon tag 105 affixed to the mobile-location asset, etc.).

In the illustrated example, when a mobile-location asset is classified as relatively-far, the example RTLS server 155 of FIG. 1 discards the reader message 130 and the RTLS server 155 makes not change to the location of the mobile-location asset and/or the asset-location confidence score associated with the mobile-location asset. For example, the reader badge 125 may have collected a relatively weak beacon message emitted from a mobile-location asset passing through the hallway outside of the patient room #1. In some examples, the reader badge 125 may filter such beacon messages (e.g., beacon messages 110 that are associated with weak (e.g., low) RSSI values, etc.) rather than communicate the weak beacon messages to the RTLS server 155.

When a mobile-location asset is classified as a relatively-immediate asset, high signal strength (e.g., an RSSI value greater than (−40) decibels, etc.) may be indicative of a mobile-location asset that is in-front of the hospital worker 126, is being used by the hospital worker 126 and/or is being moved by the hospital worker 126. In some such instances, the location of the mobile-location asset may be assumed to be the same as the location of the reader badge 125. In the illustrated example, the example RTLS server 155 of FIG. 1 updates the location of the mobile-location asset to the location of the reader badge 125. In addition, the example RTLS server 155 increments the asset-location confidence score of the mobile-location asset (e.g., the probability of the mobile-location asset being located at the updated asset-location is increased, etc.). In some examples, if the beacon tag 105 is relatively-immediate to the reader badge 125, an assumption may be made that the caregiver is interacting with the corresponding assets. For example, the caregiver may be pushing a patient in a wheelchair.

In the illustrated example of FIG. 1, when a mobile-location asset is classified as a relatively-near asset (e.g., is associated with a medium signal strength, etc.), the example RTLS server 155 of FIG. 1 compares the current location associated with the mobile-location asset to the location of the reader badge 125. In the illustrated example, the RTLS server 155 increases the asset-location confidence score of the mobile-location asset when the current asset-location is the same as the location of the reader badge 125. For example, the mobile-location asset is "seen" in the same location as it is currently assigned. In some examples when the current asset-location is not the same as the location of the reader badge 125, the example RTLS server 155 decreases the asset-location confidence score of the mobile-location asset. In addition, the example RTLS server 155 compares the asset-location confidence score of the mobile-location asset to a location threshold and, when the asset-location confidence score fails to satisfy the location threshold (e.g., is less than the location threshold, etc.), the RTLS server 155 updates the asset-location of the mobile-location asset to the location of the reader badge 125 that received the corresponding beacon message 110.

In the illustrated example of FIG. 1, the example environment 100 includes an example dock module (not shown). The example dock module may be used to charge one or more reader badges 125. In some examples, a badge in the dock module receives beacon messages 110 from beacon tags 105 and/or transmits reader messages 130 to the RTLS server 155.

Figure 2:
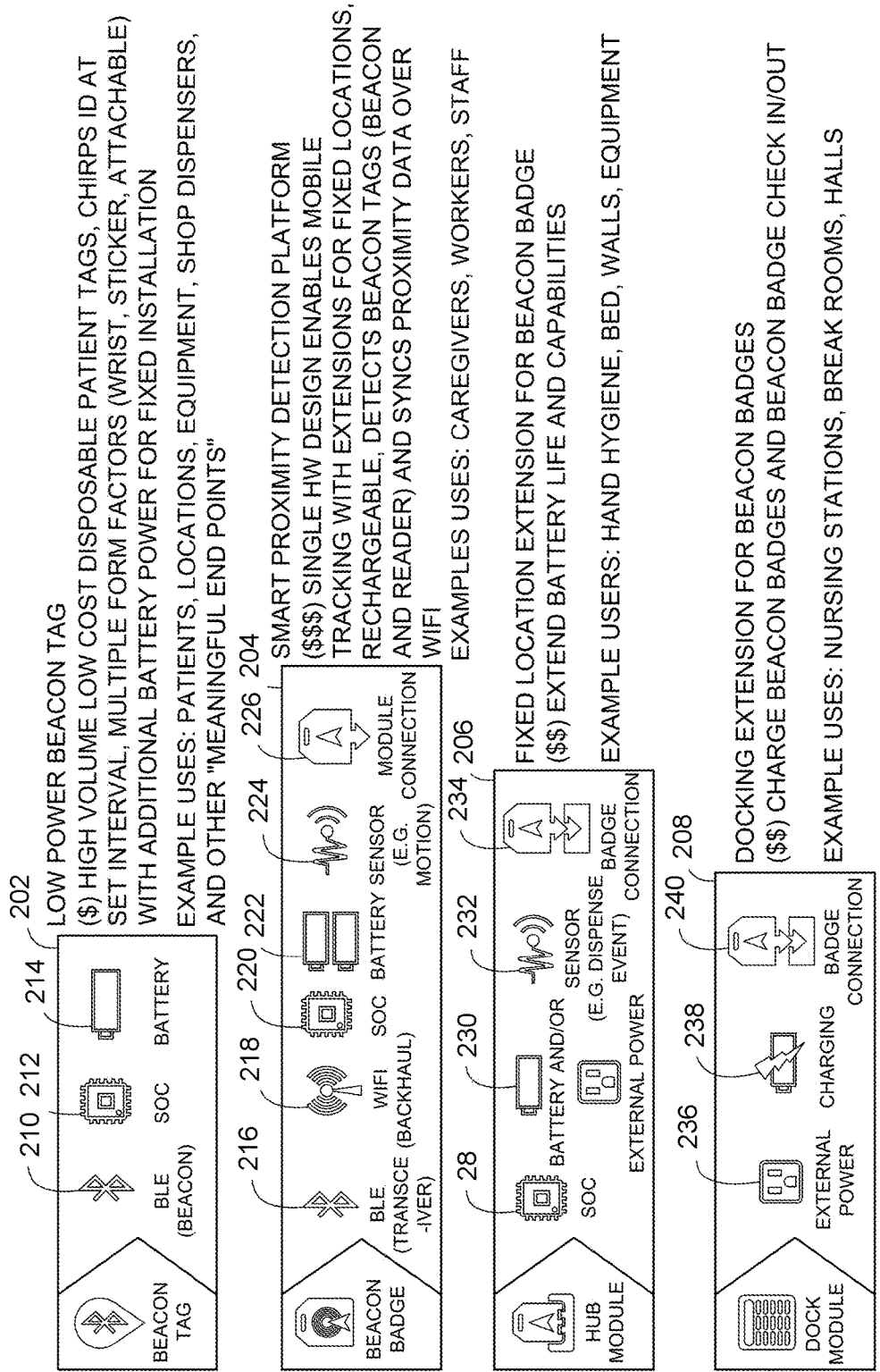
FIG. 2 illustrates various components included in an example beacon tag, an example beacon badge, an example hub module, and example dock module.

FIG. 2 illustrates various components included in an example beacon tag 202, an example beacon badge 204, an example hub module 206 and example dock module 208. For example, the beacon tag 202 includes one or more BLE chips (labeled "Beacon") 210 to transmit beacon messages 110, one or more power sources 214 (e.g., one or more coin-cell batteries, etc.) and a system-on-a-chip (SOC) 212 to manage the one or more BLE chips 210 and the one or more power sources 214. The example beacon badge 204 includes one or more BLE chips 216 (labeled "transceiver") to receive beacon messages 106a-109a, one or more Wi-Fi chips 218 to communicate with a wireless network (e.g., the example network 160, etc.), one or more power sources (e.g., one or more batteries, etc.) 222, one or more sensors 224 (e.g., a motion sensor, an accelerometer, a gyroscope, etc.) and a system-on-a-chip (SOC) 220 to manage the one or more BLE chips 216, the one or more Wi-Fi chips 218, the one or more power sources 222 and the one or more sensors 224. The example beacon badge 204 also includes an example module connector 226 to connect the beacon badge 204 to the example hub module 206 and/or the dock module 208.

In the illustrated example of FIG. 2, the beacon badge 204 is connectable to the example hub module 206 via a badge connection 234. The connection between the beacon badge 204 and the hub module 206 may include a mechanical connection, an electrical connection, or combinations thereof. In other examples, the hub model 206 is not connected to the beacon badge 204 and instead includes its own BLE and Wi-Fi backhaul similar to BLE 216 and Wi-Fi backhaul 218 to operate similarly to the beacon badge 204 (e.g., the beacon badge 204 is battery-powered while the hub module 206 is A/C current powered, etc.). In the illustrated example, the hub module 206 may be used to track asset interactions with fixed locations. In a healthcare environment, examples of fixed locations include soap dispensers, beds, walls, equipment, etc. In other environments, such as a retail environment, fixed locations may include wall sconces, light fixtures, mirrors, shelving, and other such fixed locations.

The hub module 206 may be leveraged to identify particular locations. As an example, the beacon badge 204 may be coupled, via a badge connection 234, to a hub module 206 placed on an entrance to a restricted area to identify when a person wearing a beacon tag 202 enters (or approaches) the restricted area. In one embodiment, the hub module 206 includes a system-on-a-chip (SOC) 228 to manage components of the hub module 206, one or more power sources 230 (e.g., one or more batteries and an external power source (e.g., an AC/DC connection), etc.) to extend the battery life and capabilities of the beacon badge 204, one or more sensors 232 communicatively coupled to the SOC 228, and a badge connection 234 for connecting the beacon badge 204 to the hub module 206.

In the illustrated example, the beacon badge 204 may be connectable (e.g., mechanically coupled, electronically coupled, etc.) to the example dock module 208. In the illustrated example, the dock module 208 may be used to charge one or more beacon badges 204. Accordingly, and in one embodiment, the dock module 208 includes an external power connector 236 (e.g., an alternating current (AC) connector, etc.), a charging indicator 238 to indicate whether the beacon badge 204 is charged or charging, and a badge connection 240 for connecting the beacon badge 204 to the dock module 208. In one embodiment, the dock module 208 is portable. For example, the dock module 208 may be placed throughout one or more environments, such as at cash registers, podiums, counters, nursing stations, break rooms, hallways, etc., and a caregiver may couple their beacon badge 204 to the dock module 208, via a badge connection 240, when they are off-duty. In certain examples, electronics to control the charging of the beacon badge 204 are within the beacon badge 204, and the docket module 208 serves as a power supply to charge the beacon badge 204.

Figure 3:
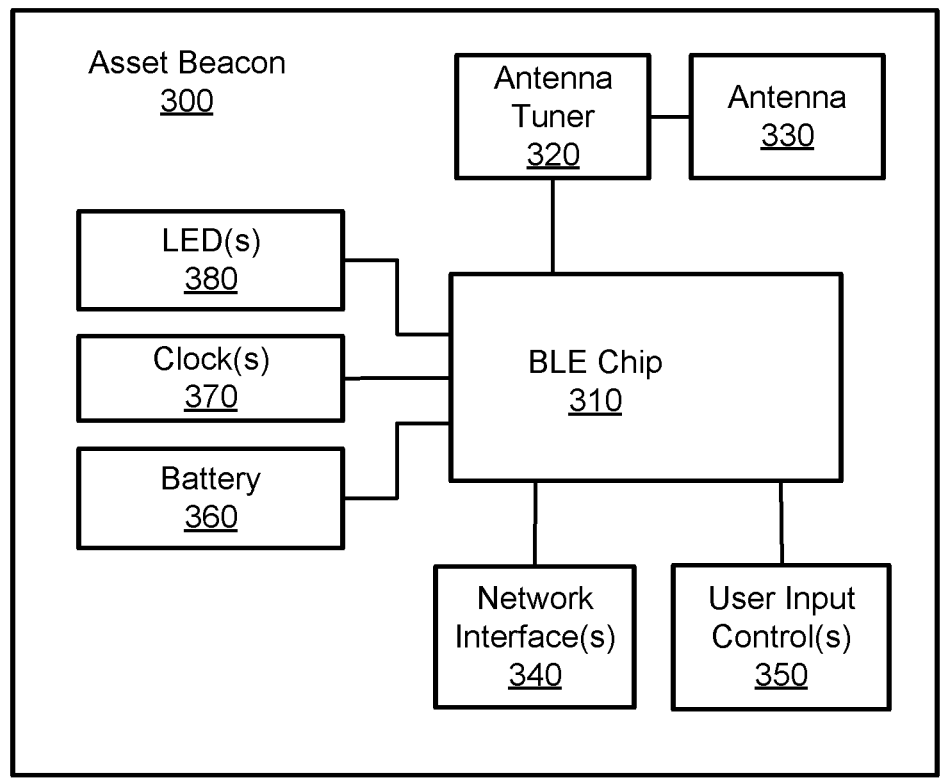
FIG. 3 is a block diagram of an example asset beacon.

FIG. 3 is a block diagram of an example asset beacon 300. The example asset beacon can be used a beacon tag 105, and/or other fixed and/or mobile asset beacon 300. The example asset beacon 300 includes a controller chip 310 (e.g., a BLE control chip 310 as shown in the example of FIG. 3, etc.), an antenna tuner 320, an antenna 330, one or more network interfaces 340, one or more user input controls 350, a battery 360, one or more clocks 370, one or more light-emitting diodes (LEDs) 380, etc.

The example beacon 300 of FIG. 3 includes the controller chip 310 to control operations for the beacon 300 including radio communication, application execution, timing, memory operation, mode/state operation, etc. As described further below, the example controller chip 310 (e.g., a TI CC26xx, TI CC13xx, etc.) can include a processor (e.g., a central processing unit (CPU), general processing unit (GPU), etc.), a radio frequency (RF) core for radio communication, sensor control, peripheral control, etc.

The example beacon 300 of FIG. 3 uses the antenna tuner 320 and associated antenna 330. In certain examples, the antenna 330 is implemented using a printed circuit board (PCB) layout antenna. In certain examples, the beacon 300 also includes debugging provisions for updating beacon code, performing diagnostic testing and optional external antenna testing via the antenna tuner 320. Antenna 330 transmit performance is dependent on the housing design as it impacts the antenna performance, for example. In certain examples, the Bluetooth antenna 330 is to collect energy from other surrounding beacons such as using an inverted F antenna configuration with ground being cleared under the antenna 330 in the beacon 300 housing.

The one or more network interfaces 340 of the example beacon 300 of FIG. 3 include a universal asynchronous receiver/transmitter (UART) communication interface, a wireless (e.g., Wi-Fi™) interface, etc. The example network interface(s) 340 can be used to facilitate communication with another device, such as the reader badge 125, etc., and/or for programming, debugging, etc. For example, the beacon 300 allows over the air (OTA) programming and parameter changes via the interface(s) 340.

The example beacon 300 of FIG. 3 includes one or more user input controls 350 such as a push button switch to activate/deactivate the controller 310, reset, change mode, etc. For example, pushing the button switches the beacon 300 between an operational mode, a connect mode, a power save/wake mode, a programming mode, etc.

The example beacon 300 of FIG. 3 includes a battery 360, such as a circular, button, or coin cell battery (e.g., CR2032, etc.) to power components of the beacon 300. The battery 360 is defined by a desired life of the beacon 300 and power the beacon 300 consumes, for example. The battery 360 can be powered to provide continuous operation of the beacon 300 for 1-2 years, for example. Battery life and/or power consumption for the beacon 300 can be impacted by transmit power (e.g., range, antenna gain, antenna power, etc.), blink rate (e.g., number of chirps per second, number of channels used during chirp, power consumption of the chirp, etc.), battery size, etc. In certain examples, the battery 360 provides one or more programmable power levels to the beacon 300.

For example, transmit power has an impact on battery life. Transmit power is defined by several factors which include range/coverage and antenna design, for example. The transmit power can be adjusted to address antenna gain and coverage for a given beacon usage. The example beacon 300 may be designed to cover a 4 to 8 feet wide aisle with a distance between beacons 4 to 8 feet. In certain examples, the antenna 330 is configured to work well when the beacon 300 is mounted against a wall or asset with a smooth surface (e.g., in a half sphere pattern, etc.) and/or (2) when the beacon 300 is hanging (e.g., via a tombstone bracket, etc.) with respect to a surface, etc.

The chirp rate indicates a number of times per second that an advertisement packet is send out by the beacon 300 (e.g., 1 beacon every two seconds, 9.5 beacons per second, 2000 millisecond (ms) chirp time, etc.). However, each additional chirp per second decreases battery life. Chirp rate is also defined by a number of channels on which the beacon 300 advertises (e.g., 2 channels, etc.). Transmitting on two channels instead of three can save power, for example.

The example beacon 300 of FIG. 3 also includes one or more clocks 370 (e.g., using a 24 MHz crystal, 32.768 kHz crystal, etc.) to support the controller 310 and radio operation via the antenna 330 and/or other interface 340 operation, for example.

The example beacon 300 of FIG. 3 uses LED(s) 380 to indicate status information. For example, the LED(s) 380 may indicate when the battery 360 charge of the beacon 300 is low, when the beacon 300 is connected to another device and/or is transmitting information, etc.

Figure 4:
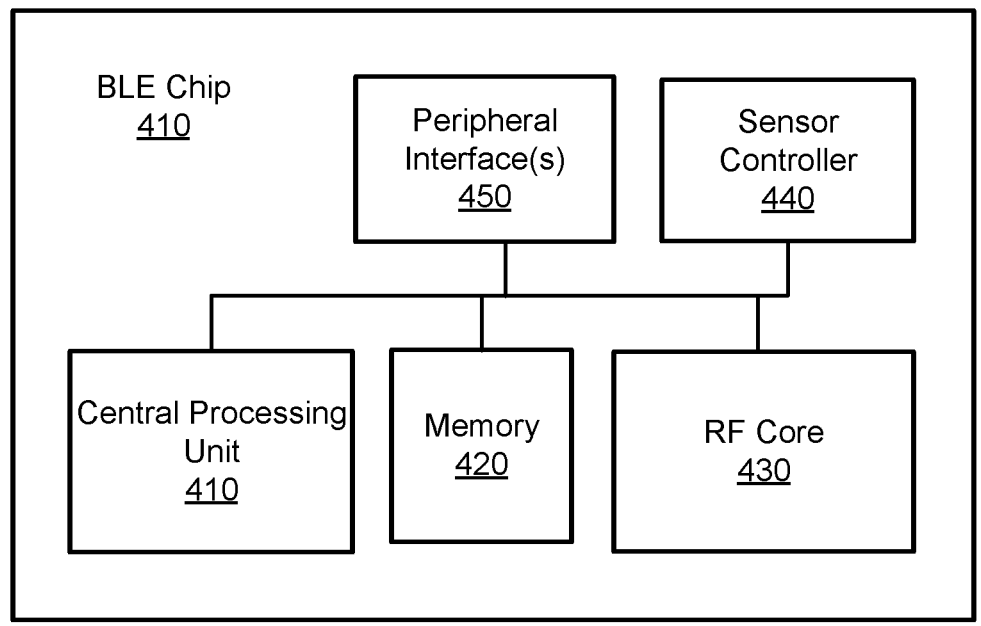
FIG. 4 illustrates an example implementation of the controller chip shown in the example of FIG. 3.

FIG. 4 illustrates an example implementation of the BLE controller chip 310 shown above with respect to the example of FIG. 3. As shown in FIG. 4, the chip 310 includes a CPU 410, a memory 420, an RF core 430, a sensor controller 440, and one or more peripheral interfaces 450.

The example CPU 410 executes instructions stored in the memory 420 to facilitate programming, testing, and operation of the BLE chip 310. For example, the chip 310 implements one or more BLE profiles and/or other low-power, short-range radio frequency wireless profiles and operates the radio (e.g., RF, etc.) with the RF core 430, clock 370, antenna tuner 320, and antenna 330. The memory 420 stores information and instructions such as a BLE protocol stack, for example, for execution by the CPU 410.

The example RF core 430 controls an RF portion of the beacon 300 radio. For example, the RF core 430 includes a phase locked loop and/or other circuit to provide carrier and modulation frequencies to generate radio signals (e.g., 2.4 GHz, 5.2 GHz, etc.). In some examples, the clock(s) 370 operate with the RF core 430 to support RF operation (e.g., to generate a beacon signal, etc.).

The example sensor controller 440 includes and/or interfaces with one or more sensors such as a low power sensor/battery monitor, a temperature sensor, etc. The example peripheral interface(s) 450 facilitate interaction with interface(s) such as the network interface(s) 340, user input control(s) 350, temperature and/or battery monitor(s), timer(s) (e.g., watchdog timer, etc.), real time clock and/or other clock 370, security module, analog comparator, etc.

Figure 5:
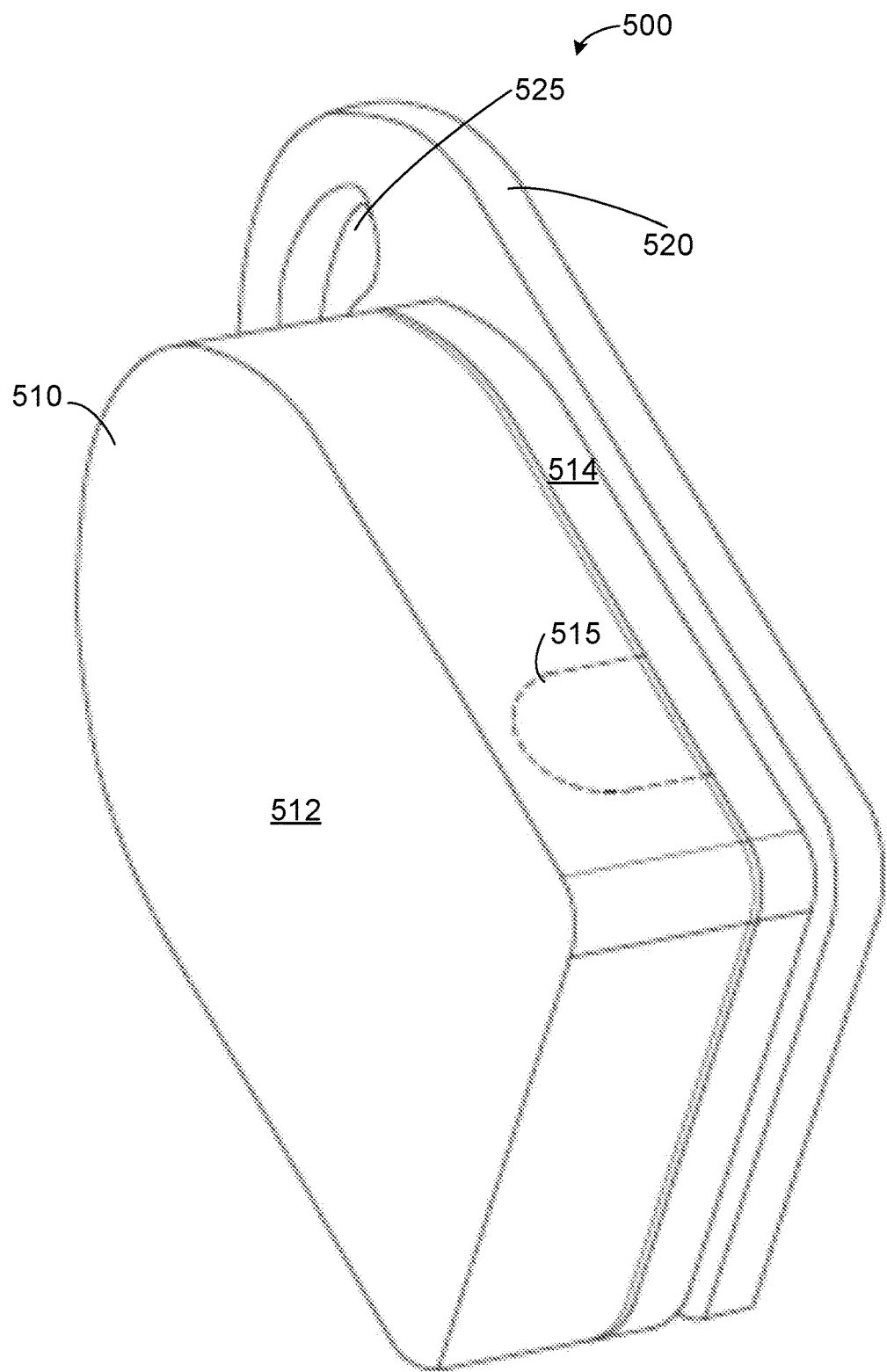
FIGS. 5-6 illustrate example beacon housings that can be used to house the example beacon of FIGS. 4-5.
Figure 6:
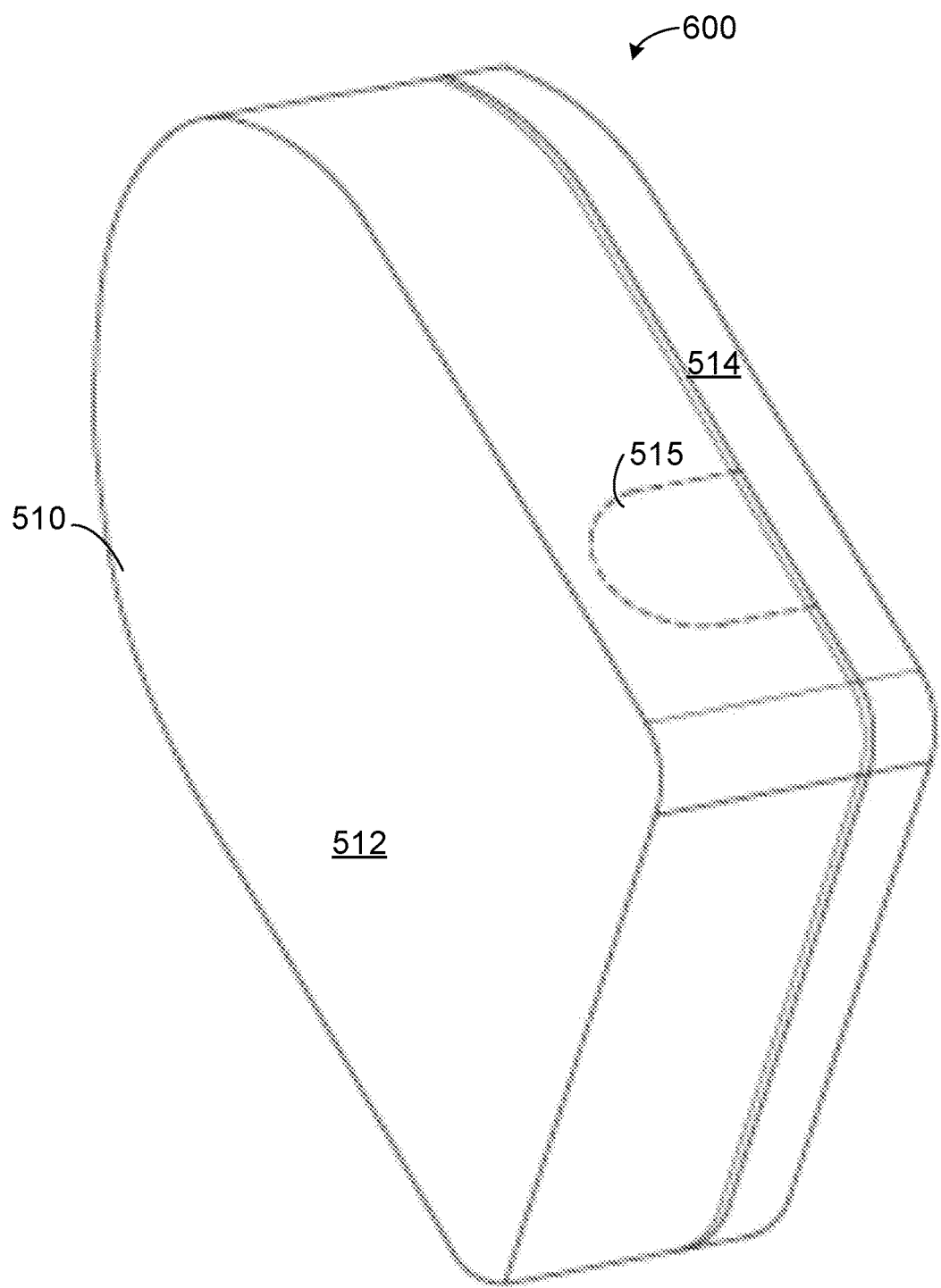

FIGS. 5-6 illustrate example beacon housings 500 that can be used to house the example beacon 300. FIG. 5 illustrates an example beacon housing 500 including a primary portion 510 and a secondary portion 520. The primary portion 510 forms the beacon 300 and encloses the components of the example beacon electronics 300 to protect the contents of the beacon electronics 300 from elements such as dirt, water, medication, cleaning fluid, germs, etc. In certain examples, the housing 510 is resistant to irradiation such as from an x-ray or computed tomography scanner, etc. The primary portion or primary housing 510 can include two sections 512, 514 that are sealed together such as using ultrasonic welding to fuse the front cover 512 and rear cover 514 together over the beacon 300 to form the primary housing 510. In certain examples, the housing 510 is removably sealed such that the housing 510 can be opened to replace the battery 360 and/or maintain other beacon 300 component(s). In other examples, the housing 510 is sealed such that it cannot be opened without damaging the housing 510 (e.g., resulting in a beacon 300 without a replaceable battery 360, etc.).

In certain examples, the primary housing portion 510 includes an opening or access port 515 through which air can flow, a push button can be inserted, an LED can be positioned, etc. In certain examples, the port or opening 515 is covered in a mesh to keep particles out of the interior of the housing 510, etc.

In certain examples, an LED and/or other light/visual indicator positioned in the opening 515 can indicate whether the beacon 300 is turned on/off, in a particular mode, etc. For example, the beacon 300 can operate in one of a plurality of modes including a shipping mode, a sleep mode, a configuration mode, an operating or normal mode, etc. The indicator and/or the beacon 300 can act differently depending on in which mode the beacon 300 is operating. For example, the indication provided by the indicator can be a different color, different pattern, flashing, etc., based on the mode. Thus, the indicator reacts differently depending upon the mode of the beacon device 300. In certain examples, the indicator can be selected through the opening 515 to change the mode of the beacon 300. The beacon 300 can be in a shipping or sleep mode in transit, a sleep mode when idle, an operating mode to emit a signal, a configuration mode to change beacon rate, etc.

In certain examples, the primary housing 510 is attached to a secondary housing 520. The secondary housing portion 520 provides a mounting surface to attach the beacon 300 to another device, surface, etc. In certain examples, the secondary portion 520 provides a plurality of mounting options including a flat surface mounting option including an adhesive such as sticky back adhesive tape located on the outward facing surface of the secondary housing 520 to be exposed by a user to attach the beacon 300 directly to a flat surface on an asset. The secondary portion 520 can provide another option for mounting using an opening 525 near and end of the secondary portion 520 which facilitates tying or wrapping of the beacon 300 to a circular structure such as a pole, cord, knob, etc., via the opening 525 of the secondary portion 520 (e.g., a tombstone shaped plastic piece, etc.).

FIG. 6 illustrates an example 600 of the primary housing 510 without the secondary housing 520. The example of FIG. 6 can be affixed to a flat surface via the primary housing 510, while the example of FIG. 5 can be affixed to a flat surface and/or a non-flat surface via the secondary housing portion 520.

In certain examples, at least one of the primary housing 510 and secondary housing 520 is transparent and/or translucent to allow the LED(s) 380 (e.g., providing an indication indicating mode, error, activity, etc.) and/or labeling of the beacon 300 to be visible through the housing 500. In other examples, one or more LEDs 380 are visible via the opening 515. In certain examples, the LED(s) 380 are integrated with and/or replaced by a button, touch key, etc., to trigger power on/off, sleep/standby, configuration, and/or other change in mode, etc. In certain examples, the primary 510 and/or secondary 520 portions of the housing 500 are cleanable without degradation or damage using one or more surface cleaners, germicidal wipes, alcohol, bleach, disinfectant cleaner, glass cleaner, hydrogen peroxide, soap, etc.

In operation, one or more way point beacons are distributed over an area in which locationing and asset tracking is desired. Asset beacons are attached to assets such as carts, products, heart pumps, scanners, etc. A hand held device with WiFi and BLE capability such as a smart phone, mobile badge, BLE/WiFi client bridge, access point with BLE sniffing, etc., can be used to detect beacons within range.

An example way point beacon sends an advertisement packet out every chirp period (e.g., 600 ms intervals, etc.). This rate can be changed such as based on a number of chirps per second needed to resolve the location with a certain accuracy and time period. Transmit power can be a variable in the operation of the beacon 300. For example, way point beacons are placed at fixed locations and the location is recorded in a locationing server in a map of the area. When the way point beacon is heard by a hand held device or one of the BLE/WiFi client bridges, the locationing server knows that the handheld device is near or in the same room as the way point beacon it is reporting. The handheld device or one of the many BLE/WiFi client bridges might also receive beacons at the same time from asset beacons. The locationing server, knowing that the mobile device has also heard a way point beacon, determines that the asset beacon(s) it is receiving are located on or near assets near or in the same room as the way point beacon. Similarly, as an asset moves around in an area, wall mount BLE/WiFi clients hear the asset's beacon come into range and out of range, allowing the locationing server to track movement of the asset. Thus, a beacon can be placed on a mobile asset and used to track that asset within a user's location, for example.

In certain examples, the beacon can transition among a plurality of modes. For example, upon power up, the asset beacon enters a connect mode. The connect mode allows the asset beacon to momentarily connect to a master BLE device, such as an Ipad™ Android™ device, etc., that, if running a toolbox application, can modify certain beacon parameters such as transmit power, chirp time, number of channels in an advertisement chirp, beacon mode and/or will also allow certain parts of the beacon's firmware to be upgraded, for example. After a time period (e.g., 20 seconds), if the beacon has not connected to a valid toolbox application, the beacon transitions to a beaconing mode. In the beaconing mode, the beacon continually chirps at a fixed rate over, for example, 1, 2 or 3 advertisement channels at the selected transmit power setting. The beacon includes a RESET switch which allows the user to change from the beaconing mode back to the connect mode, for example. This switch can also be used to put the beacon in a deep sleep where it is no longer beaconing or take the beacon out of a deep sleep, for example.

In certain examples, the asset beacon tag can be mounted in several ways. The beacon tag can be taped to equipment from the top or side, for example. The tag can also be hung on a bed, IV pole, and/or other equipment with a tie wrap or hook, for example.

Active beacons consume power (e.g., battery power, etc.) to operate. Thus, it is important to maximize and/or otherwise better leverage the available battery life of an active beacon. In certain examples, manipulation of a plurality of modes of operation can help to extend available battery life and functionality of the active beacon.

Figure 7A:
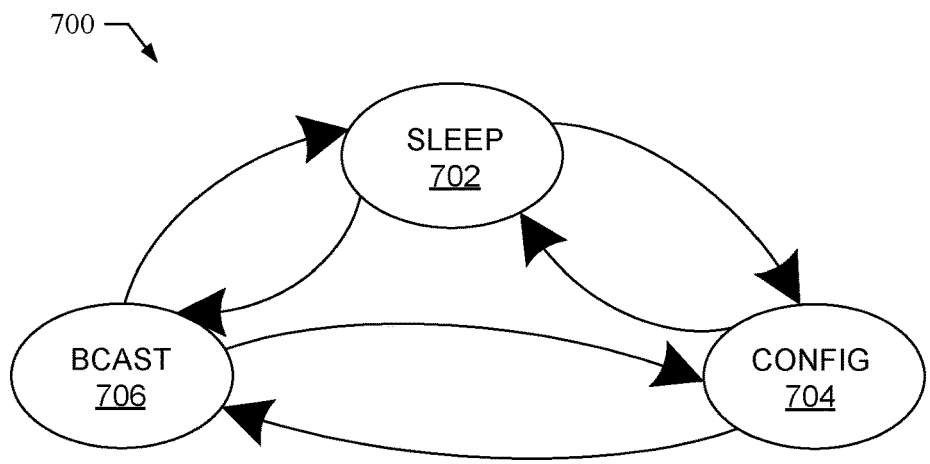
FIGS. 7A-7B illustrate example state diagrams showing transitions between states of an example beacon device.

For example, as shown in the example state diagram 700 of FIG. 7A, a beacon can operate in one or more of sleep mode 702, configuration mode 704, and broadcast mode 706. The beacon device can transition from any one mode 702-706 to another mode 702-706. For example, the beacon can transition from the sleep mode 702 (e.g., for shipping, idle, etc.) to the configuration mode 704 (e.g., to be set up and/or otherwise configured for operation in an environment, etc.). The beacon can transition from the configuration mode 704 to the broadcast or operating mode 706 (e.g., to begin broadcasting according to its configuration, etc.), for example. For example, a beacon in broadcast mode 706 can revert to the sleep mode 702 after a certain period of time without response, etc., and/or can switch to the configuration mode 704 to receive a change in configuration, further instruction, etc. A beacon in sleep mode 702 can awaken to broadcast mode 706 if already configured (e.g., with a factory or default setting, prior configuration, etc.), for example.

Figure 7B:
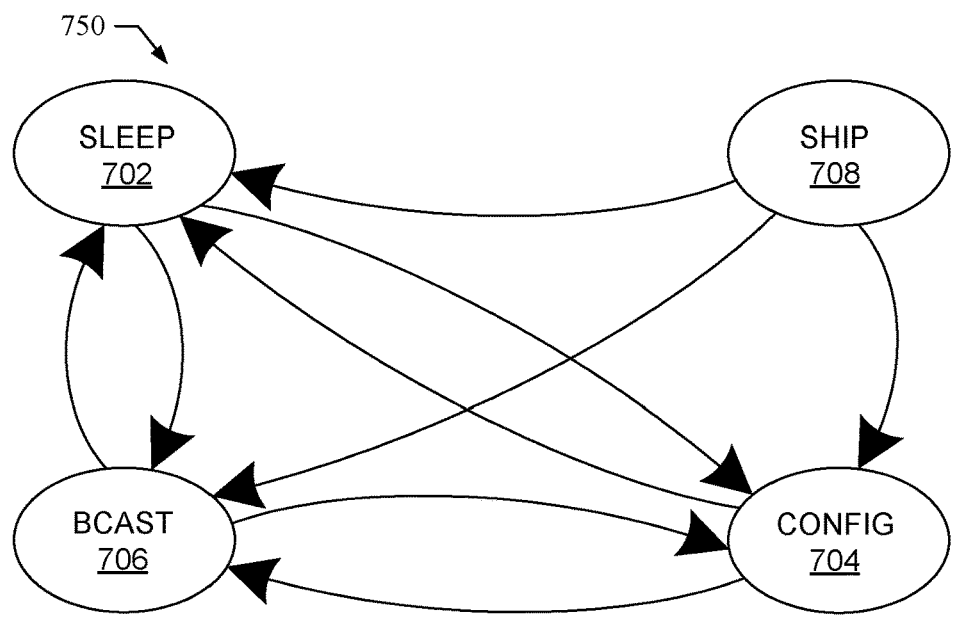

In certain examples, the sleep or idle mode 702 is distinct from a shipping or ship mode 708. A beacon device can be set in ship mode 708 from the factory and/or during transit, etc., while the sleep mode 702 can be activated at the beacon device when it is idle, etc. As shown in the example state diagram 750 of FIG. 7B, the beacon device can enter any other state 702-706 from the ship mode 708, but other modes 702-706 do not enable the beacon device to move back to the ship mode 708. However, in some examples, the beacon device can be reset by a manufacturer, supplier, administrator, etc., such as before shipping the beacon device, to reset the beacon device to factory default, reset a beacon device in an error state, etc.

In the shipping mode 708, the asset beacon device can be transported and delivered to a customer, for example. The beacon device is not transmitting or receiving communications or conducting processing during the shipping mode 708. In the sleep mode, 702, the beacon device is not transmitting or accepting client connections, for example. In the configuration mode 704, the beacon device accepts connections from clients, and clients can configure the beacon device when the client device is connected to the beacon device, for example. In the broadcast mode 706, the beacon device is transmitting data packets that conform to a supported beacon format (e.g., iBeacon, MPact, Battery Save, SecureCast, etc.), for example.

Figure 8:
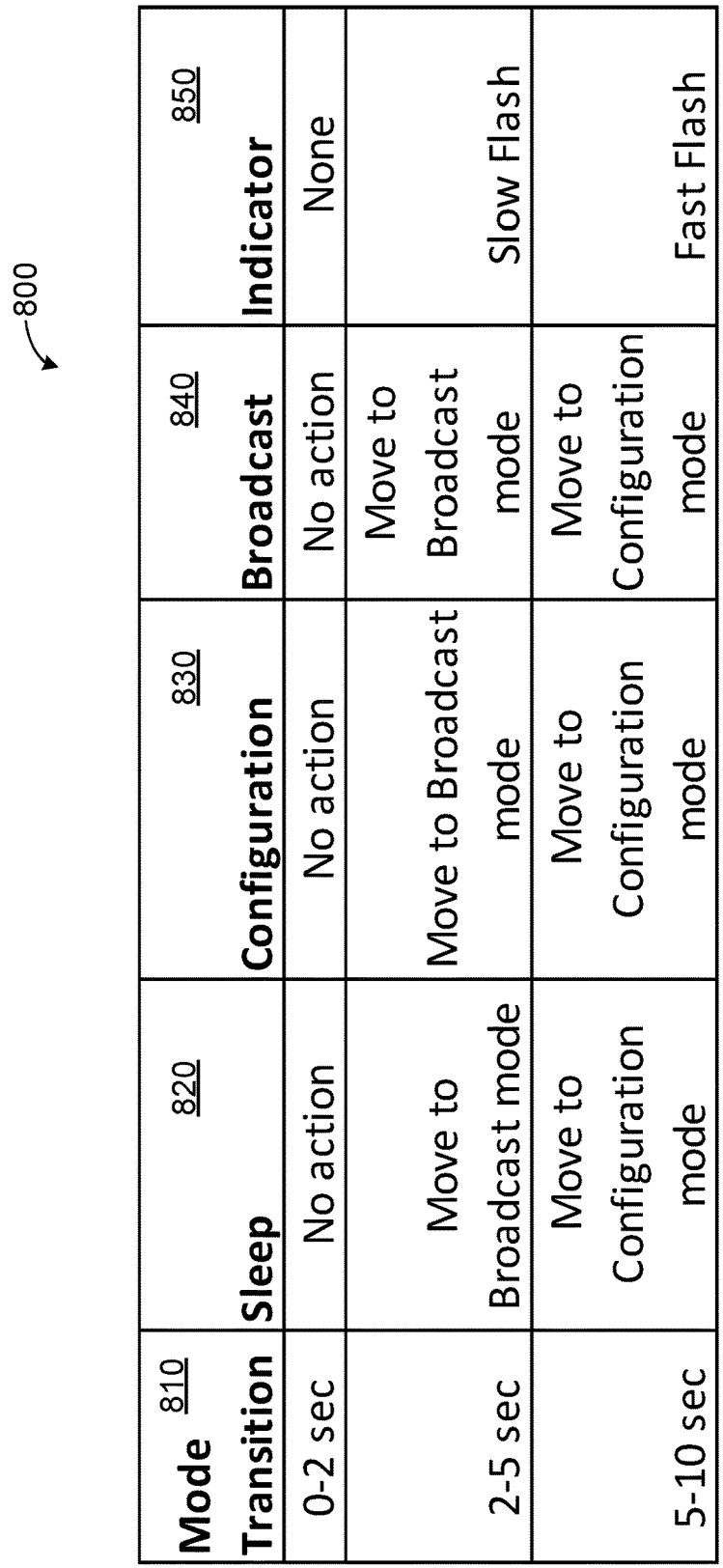
FIG. 8 illustrates an example table showing example operating modes for an example beacon device and action taken to transition the device between modes.

FIG. 8 illustrates an example table 800 showing example operating modes for an asset beacon and action taken to transition the device between modes. For example, an asset beacon can be delivered in shipping mode, and beacon operation can be initiated by pressing a button (e.g., indicator button 515, etc.) a certain number of times (e.g., one time, two times, three times, four times, etc.) and/or four a certain duration (e.g., three seconds, five seconds, ten seconds, etc.). For example, the button on or in the beacon housing 500 is pressed quickly three times and the corresponding indicator 515 flashes several times to indicate the beacon begins to broadcast.

As shown in the example chart 800, a change in operation mode 810 can be facilitated by a button press of a certain duration. For example, pressing a button on or in the beacon housing for 0-2 seconds causes no action, whether or not the asset beacon is in sleep mode 820, configuration mode 830, or broadcast mode 840, and no indication is generated via the LED and/or other indicator light 850. Pressing the button for 2-5 seconds when in sleep mode 820, configuration mode 830, or broadcast mode 840 moves the asset beacon to broadcast mode and causes the LED and/or other indicator 850 to flash slowly. Pressing the button for 5-10 seconds when in sleep mode 820, configuration mode 830, or broadcast mode 840 moves the asset beacon to configuration mode and causes the LED and/or other indicator 850 to flash quickly.

Thus, rather than beginning a usable life of an asset beacon from a date of manufacture, the beacon device's usable life begins when the device is activated by a user. The beacon device may sit in a warehouse for months, as well as sitting on a receiving dock for shipping after purchase and in an office for more months before finally being deployed. Certain examples provide the beacon device in shipping and/or sleep mode such that the beacon device does not begin using available battery power until the device is taken out of shipping/sleep mode to activate the beacon tag. Further, for conflict and confusion reasons, beacons should not be transmitting during shipment/transit (e.g., via air, water, road, etc.), and ship/sleep mode prevents the beacon device from emitting any signal until the device is activated, for example.

While typical asset beacons have a single mode and serve a single purpose with a single set of functionality, certain examples provide a configurable asset beacon that can be configured for a variety of tasks in a variety of environments. For example, a beacon can be configured to transmit slowly (e.g., infrequently, with a slower interval, etc.) on equipment that moves infrequently. Other equipment moves frequently, and a beacon can be configured to transmit more frequently to reflect a change in position. Beacons can be configured differently using a computing device, such as a smartphone, tablet computer, laptop computer, desktop computer, smart watch, etc. While prior beacons cannot be reconfigured, especially not dynamically reconfigured, certain examples facilitate dynamic (re)configuration via a computing device to manipulate any parameter associated with the beacon (e.g., frequency, period/interval, wavelength, content (e.g., major field, minor field, etc.), power, identifier, channel, etc.). Once configured, the beacon can enter broadcast mode to operate on the last stored configuration (e.g., factory default, last custom configuration, etc.) until the beacon receives different instruction. The beacon can enter sleep mode upon a certain event such as a certain idle time, a button push on the beacon, a sleep instruction from the computing device, etc.

Figure 9:
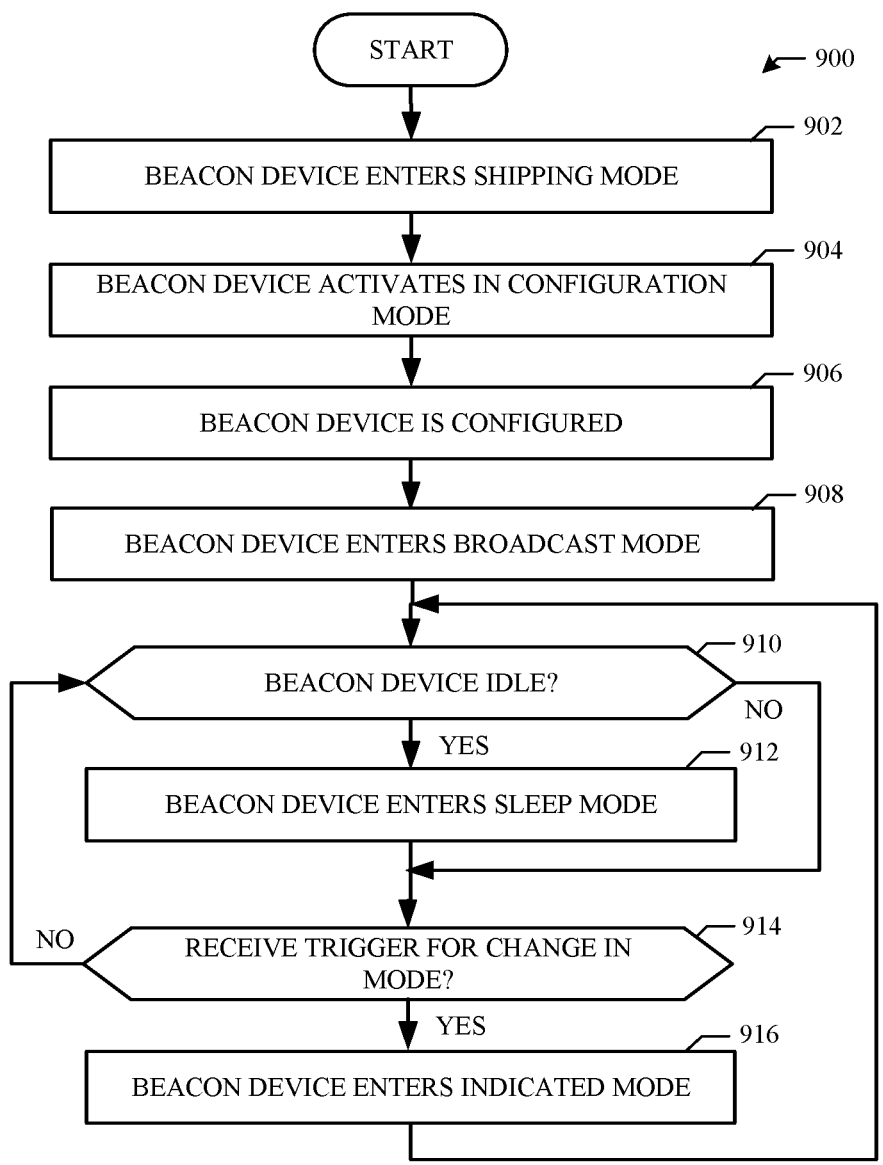
FIG. 9 illustrates a flowchart of an example method to configure an example beacon device.

FIG. 9 illustrates a flowchart of an example method 900 to configure an asset beacon. At block 902, a beacon device (e.g., beacon tag 105, 202, asset beacon 300, etc.) enters the shipping mode 708 to be shipped to a customer. For example, a manufacturer can package one or more beacon devices in shipping mode to be delivered to a hospital and/or other customer.

At block 904, the beacon device activates in the configuration mode 704. For example, upon arrival at a customer, the beacon device is turned on or otherwise activated (e.g., via a button press, toggling a switch, contacting a touch panel, moving the beacon device, etc.) in configuration mode to configure the beacon device for a purpose, use, environment, network, etc.

At block 906, the beacon device is configured. For example, a beacon device in configuration mode can interact with another device (e.g., a tablet computer, smart phone, laptop computer, smart watch, desktop computer, etc.) to receive and react to configuration information (and/or send settings, configuration confirmation, etc.). Configuration information such as power, frequency, timing, payload, identifier, etc., can be specified for the beacon device in configuration, for example.

In certain examples, the beacon device is placed in the configuration mode 704 via a first mechanism, and configuration is facilitated via a second mechanism. For example, pushing a button and/or touching a portion of the beacon device housing 500 can place the beacon device in the configuration mode 704, and configuration communication in the configuration mode 704 can occur via Bluetooth, Wi-Fi, cellular, and/or other over the air communication. For example, a configuration application running on a tablet computer with a Bluetooth communication interface can search, query, and/or listen for beacons within range that are in configuration mode 704. The tablet and/or other computing device can connect to the beacon device and transmit a new/updated configuration to the beacon from the tablet. The tablet can then reboot/restart the beacon device to activate the configuration (and place the beacon device in broadcast mode 706, etc.), for example.

In certain examples, beacon devices (e.g., Bluetooth beacon devices, etc.) are associated with an identifier, such as a universally unique identifier (UUID) (e.g., long hexadecimal, etc.). A computing device (e.g., tablet, laptop, phone, etc.) can be used as an interface to designate one or more identifiers (e.g., UUIDs) that are of interest/concern, and settings for such beacon device(s) can be adjusted in configuration. In certain examples, the UUID(s) of interest can be adjusted on a beacon in configuration. In certain examples, only a configuration application (e.g., a toolbox application, etc.) on a connected computing device can hear the beacon device in configuration mode 704 (e.g., the configuration application is listening for a particular beacon UUID, etc.).

In certain examples, a beacon device can be (re)configured to change a power level associated with the beacon device (e.g., like a knob with quieter for less power or noisier for more power, etc.). A communication protocol associated with the beacon can be configured (e.g., change Bluetooth protocol such as Apple iBeacon, Google Eddystone, Zebra MPACT, etc.). Channel usage (e.g., Bluetooth channel, etc.) can be configured (e.g., put an indication of the asset being tracked in the major field so all assets have the same major field, if the beacon is on the wall have a different major field indicating the beacon is associated with a place, etc.). For example, in a 2.4 GHz space, 37, 38, and 39 are default channels, with channel 37 on the far left of the available spectrum and channel 39 on the far right of the available spectrum, leaving 38 in the middle. In some examples, the middle of the spectrum has the most room available.

In certain examples, beacon transmit interval (e.g., 0, 10 seconds, etc.) can be (re)configured. For example, a beacon can be sent every 100 millisecond increment up to 10 seconds. In some examples, a default transmit interval is 2 seconds (e.g., every 2 seconds the beacon says hello, etc.). For example, a beacon tag on a wall advertises every 200 milliseconds. In certain examples, adjusting the transmit interval from 2 seconds to 3 seconds extends the beacon battery life by 1 year.

Once the beacon device has been configured, at block 908, the beacon device enters the broadcast mode 706. In broadcast mode 706, for example, the beacon device generates and broadcasts a signal that is received by applications associated with devices listening for an identifier (e.g., UUID, etc.) associated with that beacon, for example. Receiver(s) come on line and identify themselves to a server and request task/operating instructions from the server. The server provides beacon tags UUIDs and particular protocol(s) used by each UUID, for example. The receiver(s) listen on one or more channels and receive information from beacon tags corresponding to particular UUID(s) according to the protocol(s) specified by the server for those UUID(s), for example. The receiver(s) decompose received message(s) and relay the message(s) back to the server, to a cloud-based system, etc.

At block 910, the beacon device evaluates whether it is idle. For example, when the beacon device has received no movement for a certain period of time, no communication for a certain period of time, etc., then an operating condition of the beacon device can be determined to be idle. At block 912, the beacon device can enter the sleep mode 702 when the device is idle. For example, when the beacon device has not moved for a certain period of time, the device can consider itself idle and shift into the sleep mode 702 until awakened from its idle state (e.g., through movement, communication, instruction, etc.). In certain examples, the beacon device can enter the sleep or idle mode 702 when the device has not received a communication or otherwise interacted with another device for a certain time period. The beacon device can awake periodically from the idle mode 702 and/or await a trigger (e.g., movement, communication, contact, instruction, etc.) to awake into broadcast mode 706 from the sleep mode, for example. In the sleep/idle mode 702, the beacon device can conserve power and reduce its signal interference effect on other communications by halting its beacon signal, signaling less frequently, signaling with lower power, signaling on fewer frequencies/lower frequency range, etc. Other operating conditions impacting a transition to the sleep mode can including low power, lack of communication (transmitting and/or receiving, etc.) in a time period, etc.

In certain examples, the beacon device includes an accelerometer to automatically trigger an adjustment or reconfiguration in mode or operation of the beacon device. For example, the beacon device can be in broadcast mode 706, but movement of the device detected by the accelerometer triggers an adjustment of the beacon device into a faster mode (e.g., the beacon device is mounted on a portable imaging scanner and transmits less frequently until movement is detected to trigger more frequent beacon transmissions with the device on the move, etc.). Thus, the beacon device can have various degrees, settings, or "sub-modes" within broadcast mode 706, and/or switch between broadcast mode 706 and sleep mode 702 based on accelerometer detection of device movement, etc.

At block 914, the beacon device evaluates whether a trigger for a change in mode has been received. For example, movement of the beacon device, a tap of the beacon device, a selection of a button/switch/touchpad of the device, an instruction from an external computing device, etc., can be received to trigger a change in mode. The change in mode can be to awake the beacon device from the sleep mode 702 back to the broadcast mode 706, for example. Alternatively or in addition, the change in mode can be to place the beacon device in configuration mode 704, for example. The change in mode can be based on a combination of the trigger and/or other communication received from a receiver, controller, etc., and an operating condition of the beacon device (e.g., idle, low power, transmitting, receiving, etc.). Thus, At 916, when a trigger is received, the beacon device enters the indicated mode. For example, the beacon device can revert to broadcast mode 706, receive an instruction to transition into the configuration mode 704, receive a reset to the shipping mode 708, etc.

Figure 10:
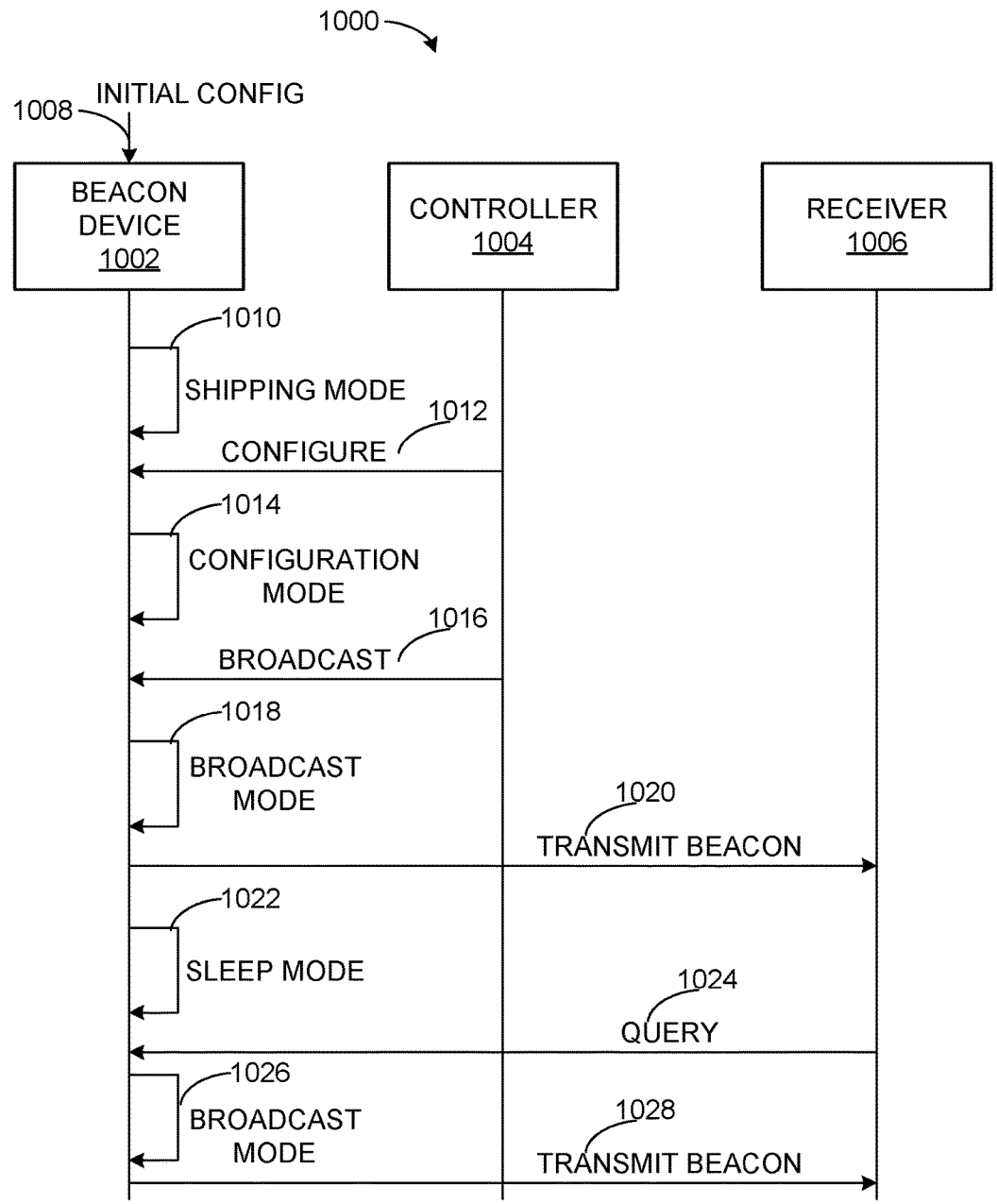
FIG. 10 illustrates a data flow diagram of an example exchange of messages and/or other instructions between an example beacon device, an example controller, and an example receiver.

FIG. 10 illustrates a data flow diagram of an example exchange of messages and/or other instructions 1000 between a beacon device 1002 (e.g., beacon tag 105, 202, asset beacon 300, etc.), a controller 1004 (e.g., RTLS server 155, tablet, smartphone, laptop, etc.), and a receiver 1006 (e.g., reader 125, badge 204, etc.). As shown in the example of FIG. 10, the beacon device 1002 receives an initial configuration 1008 (e.g., default setting, etc.) and, at 1010, is placed in the shipping mode 708. At 1012, the controller 1004 initiates a configuration of the beacon device 1002. For example, the controller 1004 at a hospital and/or other healthcare facility to which the beacon device 1002 has been delivered initiates a configuration of the beacon device 1002 for the location. At 1014, the beacon device 1002 is then in the configuration mode 704, and the controller 1004 can provide the beacon device 1002 with settings/parameters such as power level, UUID, broadcast frequency(-ies), major/minor field data payload value(s), etc. In certain examples, the beacon device 1002 is reboot and/or otherwise restarted after configuration to allow the updated settings found in the configuration information to take effect at the beacon device 1002.

At 1016, after the beacon device 1002 has been configured, the controller 1004 initiates the broadcast mode 706 at the beacon device 1002. At 1018, the beacon device 1002 operates in the broadcast mode 706. For example, in the broadcast mode 706, at 1020, the beacon device 1002 transmits beacon signal(s) to one or more receivers 1006 within range of the beacon device 1002. In certain examples, the receiver 1006 can listen for all beacon signal(s). In other examples, the receiver 1006 is configured to listen only for beacon signal(s) from the beacon device 1002 having a certain UUID and/or other identifier.

At 1022, if the beacon device 1002 i) has been idle for a certain period of time (e.g., certain hours of a day, certain passage of time without communication, certain period of time without movement, etc.), ii) is configured for a certain interval or other trigger, iii) needs to conserve power, and/or iv) other operating condition, then the beacon device 1002 enters the sleep or idle mode 702. The beacon device 1002 then enters a low power and/or otherwise low activity mode until awakened, such as by a query 1024 from the receiver 1006 to the beacon device 1002, from the controller 1004 to the beacon device 1002, time of day and/or other time elapsed at the beacon device 1002, etc. At 1026, in response to the query 1024 and/or other stimulus, the beacon device 1002 re-enters the broadcast mode 706. In the broadcast mode 706, the beacon device 1002 transmits a beacon message 1028 to the receiver 1006, for example. The beacon device 1002 can continue to operate in the broadcast mode 706 until it re-enters the sleep state 702 and/or configuration state 704, for example.

Thus, certain examples provide real time location service devices, apparatus, systems, methods, and articles of manufacture to optimize and/or otherwise improve communication, adaptability, and battery life of beacon devices (e.g., beacon tags, badges, etc.) over prior devices. Certain examples provide improved configurability of different operating conditions, tasks, applications, etc., in beacon devices over prior devices. Certain examples provide improved power management over prior beacon devices.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A low-power, short-range radio frequency wireless beacon device comprising:
    a memory to store instructions and configuration information;
    a communication interface to communicate with at least one of a receiver or a controller; and
    a processor to execute the instructions with respect to the configuration information to at least:
        control the communication interface and operation of the processor based on a mode in which the beacon device is set to operate; and
        transition dynamically among a plurality of modes after the beacon device has determined an operating condition of the beacon device, wherein the operating condition is based on a power status of the beacon device and communication activity of the beacon device with respect to at least one of the receiver or the controller,
        wherein the plurality of modes includes a configuration mode and a broadcast mode, wherein, when in the configuration mode, the operation of the processor is to process the communication received from the controller to adjust the configuration information, and, when in the broadcast mode, the operation of the processor is to generate a beacon signal to transmit to at least one of the receiver or the controller via the communication interface.

2. The beacon device of claim 1, wherein the communication interface includes at least one of an antenna or a peripheral interface.

3. The beacon device of claim 1, wherein the plurality of modes further includes at least one of a sleep mode or a shipping mode.

4. The beacon device of claim 3, wherein, when in the at least one of a sleep mode or a shipping mode, the operation of the processor includes reducing functionality to conserve power.

5. The beacon device of claim 1, wherein the operating condition includes at least one of idle, low power, transmitting, or receiving.

6. The beacon device of claim 1, wherein the processor is to transition from a first mode to a second mode in response to a first stimulus and is to transition from the first mode or the second mode to a third mode in response to a second stimulus.

7. The beacon device of claim 6, wherein the first stimulus includes a selection for a first period of time, and wherein the second stimulus includes a selection for a second period of time, the first period of time different from the second period of time.

8. The beacon device of claim 7, further including an indicator to indicate the mode of the beacon device, the indicator to provide a first indication for the second mode and to provide a second indication for the third mode.

9. The beacon device of claim 1, wherein the configuration information is to configure at least one of an identifier, a protocol, a power level, a channel usage identification, a transmit frequency, a transmit interval, or a payload for the beacon device.

10. At least one non-transitory medium including instructions which, when executed, cause at least one processor in a beacon device to at least execute the instructions with respect to configuration information to at least control a communication interface and operation of the at least one processor based on a mode in which the beacon device is set to operate and transition dynamically among a plurality of modes after the beacon device has determined an operating condition of the beacon device,
    wherein the operating condition is based on a power status of the beacon device and communication activity of the beacon device with respect to at least one of the receiver or the controller, wherein the plurality of modes includes a configuration mode and a broadcast mode, wherein, when in the configuration mode, the operation of the at least one processor is to process the communication received from the controller to adjust the configuration information, and, when in the broadcast mode, the operation of the at least one processor is to generate a beacon signal to transmit to at least one of the receiver or the controller via the communication interface.

11. The at least one non-transitory medium of claim 10, wherein the communication interface includes at least one of an antenna or a peripheral interface.

12. The at least one non-transitory medium of claim 10, wherein the plurality of modes further includes at least one of a sleep mode or a shipping mode.

13. The at least one non-transitory medium of claim 12, wherein, when in the at least one of a sleep mode or a shipping mode, the operation of the processor includes reducing functionality to conserve power.

14. The at least one non-transitory medium of claim 10, wherein the operating condition includes at least one of idle, low power, transmitting, or receiving.

15. The at least one non-transitory medium of claim 10, wherein the at least one processor is to transition from a first mode to a second mode in response to a first stimulus and is to transition from the first mode or the second mode to a third mode in response to a second stimulus.

16. The at least one non-transitory medium of claim 15, wherein the first stimulus includes a selection for a first period of time, and wherein the second stimulus includes a selection for a second period of time, the first period of time different from the second period of time.

17. The at least one non-transitory medium of claim 16, further including an indicator to indicate the mode of the beacon device, the indicator to provide a first indication for the second mode and to provide a second indication for the third mode.

18. The at least one non-transitory medium of claim 10, wherein the configuration information is to configure at least one of an identifier, a protocol, a power level, a channel usage identification, a transmit frequency, a transmit interval, or a payload for the beacon device.

19. A method of controlling a beacon device including at least one processor and a communication interface, the method comprising:

executing, using the at least one processor, instructions with respect to configuration information to at least control the communication interface and operation of the at least one processor based on a mode in which the beacon device is set to operate, and transition dynamically among a plurality of modes after the beacon device has determined an operating condition of the beacon device, wherein the operating condition is based on a power status of the beacon device and communication activity of the beacon device with respect to at least one of the receiver or the controller, wherein the plurality of modes includes a configuration mode and a broadcast mode;

when in the configuration mode, processing, using the at least one processor, communication received from the controller to adjust the configuration information; and when in the broadcast mode, generating, using the at least one processor, a beacon signal to transmit to at least one of the receiver or the controller via the communication interface.

20. The method of claim 19, wherein the processor is to transition from a first mode to a second mode in response to a first stimulus and is to transition from the first mode or the second mode to a third mode in response to a second stimulus.

* * * * *